United States Patent
Chang

(10) Patent No.: US 7,566,323 B2
(45) Date of Patent: Jul. 28, 2009

(54) SAFETY INTRAVENOUS CATHETER

(75) Inventor: Joseph J. Chang, Irving, TX (US)

(73) Assignee: Smiths Medical ASD, Inc., Rockland, MA (US)

( * ) Notice: Subject to any disclaimer, the term of this patent is extended or adjusted under 35 U.S.C. 154(b) by 741 days.

(21) Appl. No.: 09/978,457

(22) Filed: Oct. 16, 2001

(65) Prior Publication Data

US 2002/0026154 A1    Feb. 28, 2002

Related U.S. Application Data

(62) Division of application No. 09/476,429, filed on Dec. 30, 1999, now Pat. No. 6,322,537.

(51) Int. Cl.
*A61M 5/32* (2006.01)
(52) U.S. Cl. ....................................... 604/198
(58) Field of Classification Search ............... 604/162, 604/164.01, 164.08, 171, 192, 198, 263, 604/110
See application file for complete search history.

(56) References Cited

U.S. PATENT DOCUMENTS

| | | | | |
|---|---|---|---|---|
| 4,551,138 A | * | 11/1985 | Shinohara | 604/262 |
| 4,781,692 A | * | 11/1988 | Jagger et al. | 604/164.08 |
| 4,929,241 A | | 5/1990 | Kulli | |
| 4,952,207 A | | 8/1990 | Lemieux | |
| 4,964,854 A | * | 10/1990 | Luther | 604/166.01 |
| 4,978,344 A | | 12/1990 | Dombrowski et al. | |
| 5,049,136 A | | 9/1991 | Johnson | |
| 5,085,648 A | | 2/1992 | Purdy et al. | |
| 5,092,845 A | | 3/1992 | Chang | |
| 5,135,504 A | | 8/1992 | McLees | 604/164.08 |
| 5,147,327 A | | 9/1992 | Johnson | |
| 5,183,468 A | | 2/1993 | McLees | |
| 5,215,528 A | | 6/1993 | Purdy et al. | 604/164.08 |
| 5,279,591 A | | 1/1994 | Simon | |
| 5,300,045 A | * | 4/1994 | Plassche, Jr. | 604/263 |
| 5,419,766 A | * | 5/1995 | Chang et al. | 604/110 |
| 5,601,536 A | * | 2/1997 | Crawford et al. | 604/263 |

(Continued)

FOREIGN PATENT DOCUMENTS

EP    0408290    1/1991

(Continued)

*Primary Examiner*—Nicholas D Lucchesi
*Assistant Examiner*—Theodore J Stigell
(74) *Attorney, Agent, or Firm*—Wood, Herron & Evans, LLP

(57) ABSTRACT

A medical IV catheter is described comprising a needle cannula having a distal point, a proximal end and further having a shaft with a circumference, a tip protector having a base the tip protector defining an opening to receive the needle cannula shaft and the tip protector is slideably mounted thereon, means coupled to the tip protector for blocking the tip protector opening so as to enclose the needle cannula distal point within the tip protector, a gasket coupled to the tip protector base defining an opening of a size to receive the needle cannula shaft, means coupled to the needle cannula shaft impeding movement of the tip protector along the needle cannula shaft beyond a pre-determined distance from the needle cannula distal point, and a flash chamber coupled to the needle cannula at the needle cannula proximal end.

21 Claims, 2 Drawing Sheets

U.S. PATENT DOCUMENTS 6,117,108 A * 9/2000 Woehr et al. ................ 604/110
6,224,569 B1 * 5/2001 Brimhall ................ 604/164.08

FOREIGN PATENT DOCUMENTS

| EP | 0554841 | 8/1993 |
|---|---|---|
| EP | 0645159 | 3/1995 |
| EP | 0750916 | 1/1997 |

* cited by examiner

SAFETY INTRAVENOUS CATHETER

This is a divisional of Ser. No. 09/476,429, filed on Dec. 30, 1999 now U.S. Pat. No. 6,322,537.

FIELD OF THE INVENTION

This invention relates to the field of medical devices and in particular to a safety intravenous (IV) catheter.

BACKGROUND

Blood borne diseases such as AIDS and Hepatitis present significant risks to medical personnel administering vascular injections. The means by which a patient's vessel and skin are pierced to either draw or introduce fluids can just as effectively pierce the hands and arms of attending medical personnel. Gloves or similar protective garb may provide some protection, but making such items entirely resistant to needle penetration oftentimes sacrifices the wearer's mobility and dexterity proportionate to the degree of protection. Therefore, protective wear is not a total answer to the problem.

In order to adequately protect medical personnel from inadvertent puncture and wounding, catheter systems have been developed to cover and shield the distal needle point after its withdrawal from the patient. These systems have taken a number of embodiments and have various degrees of elaboration. One such mechanism includes a cylindrical sheath of plastic which telescopes out from the flash chamber to surround the needle shaft, including the distal tip. Such mechanism increases costs of manufacture substantially and may malfunction, especially in a fluid filled environment where it may stick or slip. The need for locking parts under these circumstances also increases risk of failure. Other types of needle caps require moving parts, such as a spring activation, to close off the needle in the cap after its withdrawal. These sometimes combine moving parts with specially tooled needles having two or more separate widths so that the larger circumference and diameter either trips the spring and/or blocks the needle's removal from the cap.

Given that the needle protector, however configured, will be contaminated upon each use, cost-benefit requirements dictate that a desirable shielding system be disposable along with the needle. Furthermore, the system must be quick and easy to use as to present as little imposition as possible to the administration and function of the catheter. Moving parts which may malfunction or stick such as springs and similar biasing mechanisms, as well as telescoping sheaths requiring deployment from the flash chamber, are less desirable in this regard and can drive up the manufacturing cost for a disposable unit. Lathering the needle circumference to alter the circumference over particular segments requires precise tooling and hence substantially added cost. The further requirements for sealing the system against fluid leakage and backflow may also show such designs to be problematic.

Therefore, it is desirable that a protective system be simple and dependable in its deployment, cheap to manufacture, expedient in its operation and effective in sealing off the distal point and preventing fluid leakage or backflow.

SUMMARY

A medical intravenous (IV) catheter is described comprising a needle cannula having a distal point, a proximal end and further having a shaft with a circumference, a tip protector having a base and defining an opening to receive the needle cannula shaft. The tip protector is slideably mounted on the cannula shaft. The catheter also include means coupled to the tip protector for blocking the tip protector opening so as to enclose the needle cannula distal point within the tip protector, a gasket coupled to the tip protector base defining an opening of a size to receive the needle cannula shaft, means coupled to the needle cannula shaft impeding movement of the tip protector along the needle cannula shaft beyond a pre-determined distance from the needle cannula distal point, and a flash chamber coupled to the needle cannula at the needle cannula proximal end.

Other features and advantages of the invention will be apparent from the accompanying drawings and from the detailed description that follows below.

BRIEF DESCRIPTION OF THE DRAWINGS

The invention is illustrated by way of example and not by way of limitation in the figures of the accompanying drawings in which like references indicate similar elements and in which.

DETAILED DESCRIPTION

Figure 1:
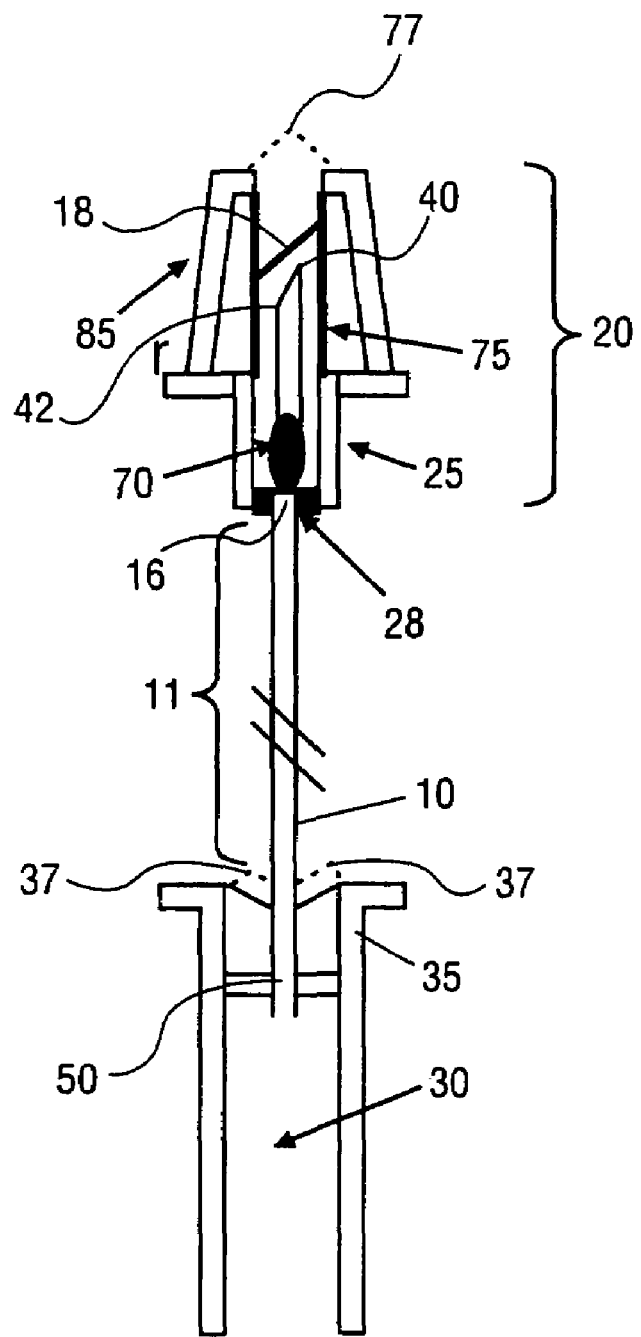
FIG. 1 shows the IV catheter apparatus according to an embodiment of the invention.

Referring to FIG. 1, depicting a catheter and needle cannula 10 including distal tip protector 20 according to the invention, tip protector 20 defines an opening 77 through which extends needle cannula 10. Tip protector 20 is slideably movable along the length of needle cannula shaft 11 from the point where needle cannula 10 engages the flash chamber 30 to a pre-determined distance from distal tip 40 of needle cannula 10. In one embodiment, flash chamber 30 includes walls 35 which define a slot 37 into which tip protector base 25 snugly fits before it is moved along needle cannula 10 toward distal tip 40. Needle cannula 10 defines a lumen pathway (not pictured) and comprises an insertion needle having pointed distal end 40. Proximal end 50 of needle cannula 10 is fixed to distal end of flash chamber 30 so as to be in fluid communication therewith. Needle cannula 10 may be affixed by adhesive such as epoxy to form a plug sealing flash chamber 30. Needle cannula 10 may also be affixed to the flash chamber 30 and sealed thereon by other ways known in the art.

Tip protector 20 has, at its proximal end, tip protector base 25 coupled to a superstructure 85 which together define the opening 77 through which needle cannula shaft 11 extends. At tip protector base 25, where needle cannula shaft 11 extends into the tip protector 20 from its proximal end 50, a gasket 28 surrounds the needle cannula shaft 11 and creates an opening almost identical in circumference to needle cannula shaft 11. In one embodiment, the gasket is formed in place to seal the opening, yet allowing the needle cannula 10 to slide therethrough; in one embodiment this may be further assisted by the application of lubricant to needle cannula shaft 11. An example of suitable lubricant may be silicone in a hexane solvent applied by spraying or dipping. Suitable gasketing material may include adhesive such as LV3021-69, an ultraviolet (UV) curable acrylic base material available from Loctite, Inc. An ultraviolet cured cured adhesive is desirable for its rapid curing in a high volume manufacturing process and its ability to form a 100% solid gasket. Application of the adhesive and ultraviolet exposure may be accomplished by methods known in the art (for instance in the manner described in U.S. Pat. No. 5,092,845). Other suitable adhesives that may act as gaskets include paraffin-polyester or polyamide-type material.

At a pre-determined distance from the distal tip 40 of needle cannula 10, a crimp 70 is made into the needle cannula shaft 11 which may be located in one embodiment between 0.05"-0.15"below heel 42 of distal point 40. Crimp 70 may be simply a deformity in the uniform circumference of the needle cannula shaft 11, collapsing the cannula needle lumen diameter (not pictured), but not closing off the needle cannula lumen. Crimp 70 may be stamped upon the needle surface by machining techniques known in the art. In one embodiment, crimp 70 compresses the uniformly circular needle cannula shaft 11, giving it an irregular or basically oval cross-sectional shape. In one embodiment, the compression does not seal the lumen, but merely elongates it so that the area of the lumen through which fluid passes is unchanged and fluid flow unimpeded. As an alternative to a crimp in needle cannula shaft 11, a protuberance may be formed on the outer surface of needle cannula shaft 11, such as by soldering or pressure fitting a durable O-ring around needle shaft 11.

In its irregular or oval shape, the needle cannula shaft 11 outer diameter is lengthened in one direction, i.e., the compression diameter. This lengthening prevents needle cannula shaft 11, and hence distal point 40, from being removed through the opening at tip protector base 25 defined by gasket 28. The circular gasket opening is nearly equivalent to the diameter and circumference of needle cannula shaft 11 when uniformly circular. Needle cannula crimp 70 compression diameter exceeds that of the gasketed opening and prevents further movement of the tip protector 20 along the needle cannula shaft 11 toward the distal point 40. Thus crimp 70 prevents the tip protector from being moved the entirety of needle cannula 10 length and hence prevents its removal from its position covering distal tip 40 of the needle cannula 10.

Thus, the tip protector 20 slides from a proximal location where the tip protector base 25 is received within slot 37 defined by walls 35 of flash chamber 30, along needle cannula shaft 11 to the point where crimp 70 on needle cannula shaft 11 blocks the opening of gasket 28, thus preventing further movement of tip protector 20 along needle cannula shaft 11. The positioning of crimp 70 on needle cannula shaft 11 is predetermined so that when crimp 70 engages gasket 28, tip protector superstructure 85 covers distal end 40 of needle cannula 10. Resiliently mounted within tip protector superstructure 85 in the passage occupied by needle cannula shaft 11 is tab 18 removing the impediment of needle cannula shaft 11. The presence of needle cannula shaft 11 in tip protector superstructure 85 holds tab 18 in a stressed position against shaft 11. Once distal tip 40 of needle cannula 10 is drawn below the level of tab 18, the tab is free to pivot across the opening 77 of tip protector superstructure 85 blocking needle cannula distal tip 40 from re-emerging from tip protector 40 which now covers it.

Tab 18 is substantially of the type described in U.S. Pat. No. 5,419,766. It is stamped and formed of stainless steel metal and heat treated to create a resilient property or spring action in order that the tab, if biased or stressed, retains memory to return to a flexed position.

Tab 18 is located a pre-determined distance from the top opening of the tip protector superstructure 85 so that distal tip 40 of needle cannula 10 passes tab 18, releasing the tab to pivot and block the top opening of superstructure 85, before the crimp 70 engages gasket 28 opening at tip protector base blocking further movement of tip protector 20 along needle cannula shaft 11. As an illustration, in one embodiment, tip protector superstructure 85 may have an overall length of approximately 0.250 inches and tab 18 may be located approximately between 0.03 inches and 0.07 inches from the top opening of tip protector superstructure 85. Thus, preferably tip protector 20, from superstructure 85 to base 25, will be a predetermined length so as to encompass needle cannula 10 from its distal tip 40 to crimp 70, within tip protector 20.

Figure 2:
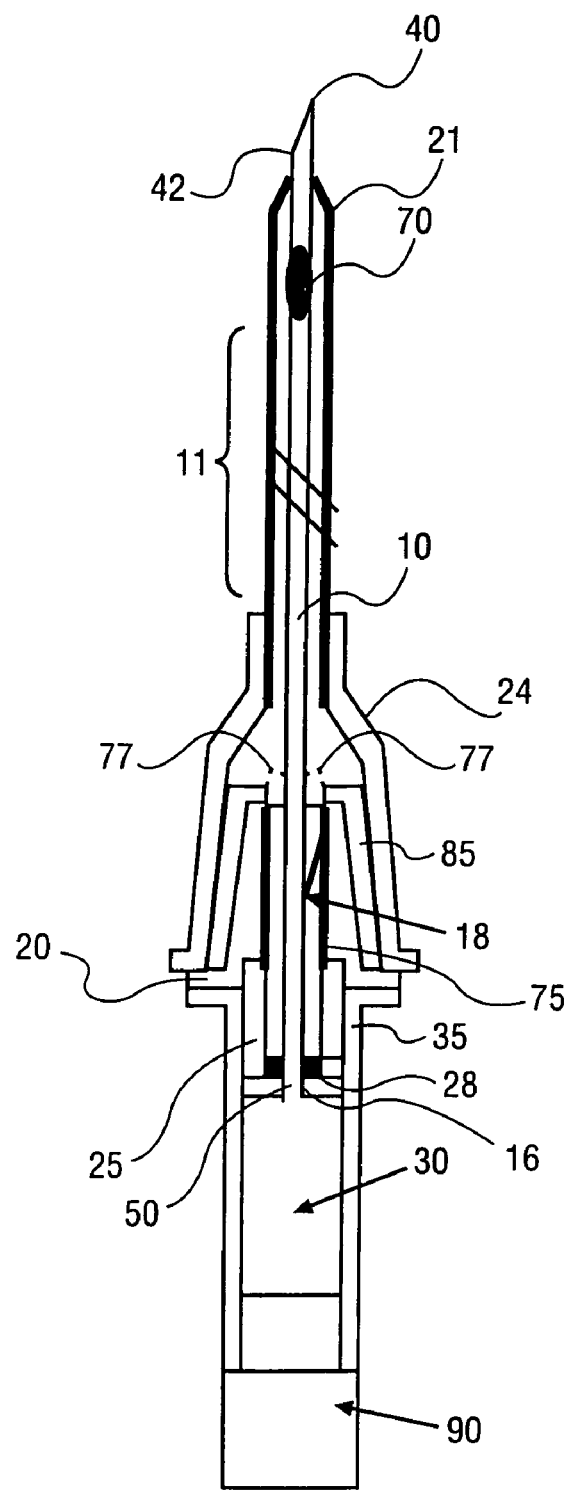
FIG. 2 shows the IV catheter apparatus according to an embodiment of the invention as employed with catheter cover and hub.

FIG. 2 illustrates an embodiment of the invention as used with a catheter assembly. Catheter 21 sheathes the needle cannula 10, where the needle cannula distal point 40 extends beyond the catheter sheath to make the incision. Catheter 21 then provides the lumen which maintains fluid communication with the patient after distal tip 40 of needle cannula 10 is withdrawn. Catheter hub 24 fits over tip protector 20 while tip protector base 25 fits within flash chamber slot 37, defined by flash chamber walls 35. Flash plug 90, is coupled to flash chamber 30 proximate end of flash chamber 30 partially sealing the chamber. Flash plug 90, in one aspect, vents air accumulated through venipuncture, permitting back flow of blood into the chamber as appropriate, while containing blood within flash chamber 30.

In one embodiment, the invention operates as follows: when needle cannula distal tip 40 and catheter distal tip 22 is inserted into a patient and fluid communication is established with flash chamber 30, tip protector 20 remains coupled to flash chamber 30 which receives tip protector base 25 tucked inside slot 37 defined by flash chamber walls 35. Upon completion of the insertion, the catheter 21 and catheter hub 24 are left as inserted, distal tip 40 of needle cannula 10 is removed and withdrawn gradually through catheter 21 and catheter hub 24. Meanwhile, tip protector 20 is manually slid along the length of needle cannula shaft 11. At approximately the point where gasket 28 defining the tip protector base opening 16 engages needle cannula crimp 70, blocking further movement of protector tip 20 along needle cannula shaft 11, distal tip 40 of needle cannula 10 slides below biased tab 18 pressing against needle cannula 10, thus removing the resistance to the tab bias. Tab 18, now free to move, then pivots to block the tip protector opening 77, sealing distal tip 40 within tip protector 20. Where distal tip 40 of needle cannula 10 is prevented from re-emerging from tip protector superstructure 85, needle cannula crimp 70 prevents tip protector 20 from sliding further up needle cannula shaft 11 and off distal tip 40. At such time the apparatus can be safely handled and disposed of by medical personnel, with catheter 21 and catheter hub 24 remaining with the patient.

In one embodiment, tab 18 is metal that is part of metal clip 75 housed within tip protector superstructure 85 and defining opening 77 as a through hole through which needle cannula shaft 11 extends when in operation. Through hole 77, typically will have a diameter slightly greater than the needle cannula shaft 11 outer diameter and will vary depending on the needle gauge used. Metal clip 75 may be made from a cylindrical piece of metal such as tube stock which has tab 18 punched therein and bent toward the inside of cylindrical metal clip 75. Tab 18 is formed by being cut from the clip cylinder interior, heat treated for spring action, and pressed inward, retaining an elastic bias or memory to flex outwards and across through hole 77. Tab 18, in this embodiment, thus may be formed from metal clip 75, at a point intermediate the clip cylinder or may extend all of the way to the end of the cylinder so long as the length of the cut creating tab 18 enables the tab to flex outward and across through hole 77, so as to either bridge the opening entirely or to block movement of the needle cannula shaft therethrough.

Retraction of distal tip 40 of needle cannula 10 into metal clip 75 portion below the level of tab 18 releases the biased tab 18 which flexes to close through hole 77 of metal clip 75 over distal tip 40. Metal clip 75 may include a windowed opening (not pictured) on the cylinder through which, where tip protector superstructure 85 is fashioned from a transparent material, immobilized needle cannula distal tip 40 may be viewed to ensure the tip is fully within tip protector 20 and thus safely covered.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. An apparatus comprising:
    a needle cannula having a distal point, a proximal end and further having a shaft with a circumference;
    a tip protector having a base, the tip protector defining an opening to receive the needle cannula shaft and the tip protector is slideably mounted thereon;
    blocking means coupled to the tip protector for blocking the tip protector opening so as to enclose the distal point of the needle cannula within the tip protector;
    a gasket coupled to the tip protector base defining an opening nominally of a size almost identical to the shaft circumference to receive the needle cannula shaft;
    impeding means fixedly coupled to the needle cannula shaft at a predetermined location of the shaft and defining a size larger than the shaft circumference and the gasket opening for impeding movement of the tip protector along the needle cannula shaft beyond a pre-determined distance from the needle cannula distal point.

2. The apparatus of claim 1 further comprising a flash chamber coupled to the needle cannula at the needle cannula proximal end.

3. The apparatus of claim 1, wherein the gasket is formed in place at the tip protector base of an adhesive material.

4. The apparatus of claim 3, wherein the gasket adhesive material is selected from the group consisting of paraffin, polyester and polyamide.

5. The apparatus of claim 3, wherein the gasket adhesive material is cured by exposure to ultraviolet light.

6. The apparatus of claim 1 wherein the blocking means comprises:
    a tab having a length sufficient to block the tip protector opening, the tab pivotably coupled to the tip protector within the tip protector opening and slideably engaging the needle cannula shaft in a first biased position such that upon removal of the needle cannula shaft the tab is free to pivot to a second position extending across the tip protector opening.

7. The apparatus of claim 6, wherein the tab is an anti-stick metal tab.

8. The apparatus of claim 6, wherein the tip protector further comprises:
    a superstructure coupled to the base;
    a cylindrical anti-stick metal clip housed within the superstructure defining an opening to receive the needle cannula shaft, the clip housing the tab, the tab disposed within the clip opening such that in its first position the tab is biased against the needle cannula shaft and in its second position the tab pivots to block the clip opening.

9. The apparatus of claim 8, wherein the tip protector is optically transparent, the cylindrical clip opening is a first opening, and the clip further defines a second opening extending over a portion of the cylindrical circumference exposing a portion of the first opening.

10. The apparatus of claim 1 wherein the impeding means comprises:
    an irregularity in the needle cannula shaft circumference a pre-determined distance from the needle cannula distal point occluding passing of the needle cannula shaft through the gasket opening.

11. The apparatus of claim 10, wherein the irregularity is a crimp inscribed in the needle cannula shaft.

12. An apparatus comprising:
    a needle cannula having a distal point, a proximal end and further having a shaft with a circumference;
    a tip protector having a proximal base with a proximal opening and a distal end defining a distal opening, the needle shaft movable through the proximal and distal openings along a path between a first position with the distal point projecting distally beyond the distal end of the tip protector and a second position with the distal point proximally behind the distal end in the tip protector;
    a member coupled to the tip protector and moveable into the path between the distal point and the distal opening with the needle shaft in the second position so as to block the distal opening; and
    a separate gasket coupled to the tip protector base proximal opening and defining a gasket opening nominally of a size almost identical to the shaft circumference and through which the needle shaft is movable between the first and second positions;
    an irregularity in the needle cannula shaft circumference a pre-determined distance from the needle cannula distal point and defining a size larger than the shaft circumference and the gasket opening occluding passing of the needle cannula shaft through the gasket opening.

13. The apparatus of claim 12, the proximal opening sized to pass the irregularity therethrough.

14. The apparatus of claim 12 further comprising a flash chamber coupled to the needle cannula at the need cannula proximal end.

15. The apparatus of claim 12, the gasket being a formed in place gasket.

16. The apparatus of claim 12, the gasket being comprised of an adhesive material.

17. The apparatus of claim 16, wherein the gasket adhesive material is selected from the group consisting of paraffin, polyester and polyamide.

18. The apparatus of claim 16, wherein the gasket adhesive material is cured by exposure to ultraviolet light.

19. The apparatus of claim 12, the member being pivotably coupled to the tip protector and slideably engaging the needle cannula shaft until the needle shaft is in the second position so as to be out of the path while the needle cannula moves from the first position toward the second position, the member pivoting into the path between the distal point and the distal opening with the needle shaft in the second position.

20. The apparatus of claim 12, the irregularity in the needle cannula shaft circumference being a crimp.

21. The apparatus of claim 12, the member being an anti-stick metal tab.

* * * * *

UNITED STATES PATENT AND TRADEMARK OFFICE
CERTIFICATE OF CORRECTION

PATENT NO. : 7,566,323 B2
APPLICATION NO. : 09/978457
DATED : July 28, 2009
INVENTOR(S) : Joseph J. Chang It is certified that error appears in the above-identified patent and that said Letters Patent is hereby corrected as shown below:

Column 2
line approximately 63, "cured cured adhesive" should be -- cured adhesive --

Claim 14
Column 6, line 40, "at the need cannula" should be -- at the needle cannula --

Signed and Sealed this

Sixteenth Day of February, 2010

David J. Kappos
*Director of the United States Patent and Trademark Office*